United States Patent
Zaiser et al.

(10) Patent No.: US 7,591,266 B2
(45) Date of Patent: Sep. 22, 2009

(54) HYBRID ELECTRO-PNEUMATIC CONSERVER FOR OXYGEN CONSERVING REGULATOR

(75) Inventors: LeNoir E. Zaiser, Naples, FL (US); Kevin Confoy, Naples, FL (US)

(73) Assignee: Inovo, Inc., Naples, FL (US)

( * ) Notice: Subject to any disclaimer, the term of this patent is extended or adjusted under 35 U.S.C. 154(b) by 675 days.

(21) Appl. No.: 10/772,220

(22) Filed: Feb. 4, 2004

(65) Prior Publication Data
US 2005/0039752 A1 Feb. 24, 2005

Related U.S. Application Data

(60) Provisional application No. 60/444,995, filed on Feb. 4, 2003.

(51) Int. Cl.
*A61M 16/00* (2006.01)
(52) U.S. Cl. .............. 128/205.24; 128/204.26
(58) Field of Classification Search .......... 251/30.01, 251/30.05; 128/205.24, 205.18, 205.22, 128/204.18, 204.21, 204.26, 204.27, 203.24; 137/908

See application file for complete search history.

(56) References Cited

U.S. PATENT DOCUMENTS

| | | | | |
|---|---|---|---|---|
| 4,736,750 A | * | 4/1988 | Valdespino et al. | 600/538 |
| 4,738,283 A | * | 4/1988 | Shirai et al. | 137/624.11 |
| 4,789,143 A | * | 12/1988 | Smith et al. | 267/140.14 |
| 4,932,402 A | * | 6/1990 | Snook et al. | 128/204.23 |
| 5,038,774 A | | 8/1991 | Chabert | |
| 5,479,920 A | * | 1/1996 | Piper et al. | 128/204.23 |
| 6,036,445 A | * | 3/2000 | Reynolds | 417/53 |
| 6,116,242 A | | 9/2000 | Frye et al. | |
| 6,170,526 B1 | * | 1/2001 | O'Neill | 137/625.65 |
| 6,364,161 B1 | | 4/2002 | Pryor | |
| 6,427,967 B1 | * | 8/2002 | Evans | 251/26 |
| 6,793,199 B2 | * | 9/2004 | Bushik et al. | 251/367 |
| 2004/0154693 A1 | | 8/2004 | Zaiser et al. | |

\* cited by examiner

*Primary Examiner*—Steven O Douglas
(74) *Attorney, Agent, or Firm*—The Johnson IP Law Firm; Rodney D. Johnson

(57) ABSTRACT

A gas regulator includes a slave valve assembly for receiving and controlling the flow of gas to a desired destination. A timing chamber is positioned adjacent to the slave valve assembly. The timing chamber has an inlet for also receiving the gas. An electronically operated pilot valve assembly is in communication with the timing chamber for operating the slave valve assembly. When the pilot valve assembly is closed, gas pressure within the timing chamber acting on the slave valve assembly closes the slave valve assembly. When the pilot valve assembly is open, gas exits the timing chamber and reduces the gas pressure in the timing chamber, thereby allowing the slave valve assembly to open and deliver the gas to the desired destination.

49 Claims, 4 Drawing Sheets

HYBRID ELECTRO-PNEUMATIC CONSERVER FOR OXYGEN CONSERVING REGULATOR

RELATED APPLICATION

This application claims the benefit of U.S. Provisional Application No. 60/444,995, filed Feb. 4, 2003. The entire teachings of the above application are incorporated herein by reference.

BACKGROUND

Gas-conserving regulators include oxygen regulators, which are used to supply a patient with a regulated flow of oxygen. The oxygen is supplied by a source of compressed oxygen, such as from a supply tank, which has its pressure reduced to a low pressure for delivery to the patient. Typical oxygen regulators employ a back-pressure piston to supply a continuous flow of that low pressure oxygen to the patient. Much of that oxygen is wasted because it is not inhaled by the patient.

To reduce the amount of wasted oxygen, oxygen-conserving regulators have been developed which tend to limit the oxygen flow to periods of inhalation. One way of controlling the oxygen flow is by electronic means. In a typical electronic conserver, a solenoid valve controls the flow of oxygen to the patient. The solenoid valve can accurately open to provide the flow of oxygen to the patient when the patient inhales, and close between breaths. Typically, the solenoid valve requires large energy requirements so that a C or D sized battery powering the solenoid valve might last only one month.

SUMMARY

Embodiments of the present invention include a gas conserving regulator which can deliver gas to a patient with the accuracy of an electronic conserver, but with significantly reduced energy consumption so that batteries can last much longer or can be smaller.

One embodiment includes a gas regulator including a slave valve assembly for receiving and controlling the flow of gas to a desired destination. A timing chamber can be positioned adjacent to the slave valve assembly. The timing chamber has an inlet for also receiving the gas. An electronically operated pilot valve assembly can be in communication with the timing chamber for operating the slave valve assembly. When the pilot valve assembly is closed, gas pressure within the timing chamber acting on the slave valve assembly closes the slave valve assembly. When the pilot valve assembly is open, gas exits the timing chamber and reduces the gas pressure in the timing chamber, thereby allowing the slave valve assembly to open and deliver the gas to the desired destination.

In particular embodiments, the gas is oxygen which is delivered to a patient. A sensing circuit can sense inhalation by the patient for controlling the electronically operated pilot valve assembly.

The slave valve assembly can include a slave valve nozzle and a slave valve member for engaging the slave valve nozzle. The gas pressure within the timing chamber acting on the slave valve member can control the operation of the slave valve member, which can be a diaphragm.

In one embodiment, the electronically operated pilot valve assembly can include a piezoelectric device. In another embodiment, the electronically operated pilot valve assembly can be a solenoid operated pilot valve assembly.

The solenoid operated pilot valve assembly can include a pilot valve nozzle and a pilot valve member for engaging the pilot valve nozzle. A solenoid operates the pilot valve member. A spring can be used to bias the pilot valve member towards the pilot valve nozzle to be normally closed. The pilot valve nozzle and the pilot valve member can be aligned along a common axis whereby the pilot valve member moves along the axis for engaging and disengaging from the pilot valve nozzle.

The timing chamber and the solenoid operated pilot valve assembly can be positioned within a common housing with the timing chamber and the pilot valve nozzle being connected by a passage therebetween. The slave and pilot valve nozzles each have an opening where the pilot valve nozzle opening can be smaller than the slave valve nozzle opening for minimizing the solenoid size and energy expended by the solenoid. The slave and pilot valve nozzle openings can be sized to provide at least about a 45:1 area and solenoid energy efficiency ratio. For such a ratio, the slave valve nozzle opening can be at least about 0.048 inches in diameter and the pilot valve nozzle opening can be about 0.007 inches in diameter.

BRIEF DESCRIPTION OF THE DRAWINGS

The foregoing and other objects, features and advantages of the invention will be apparent from the following more particular description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

Figure 1:
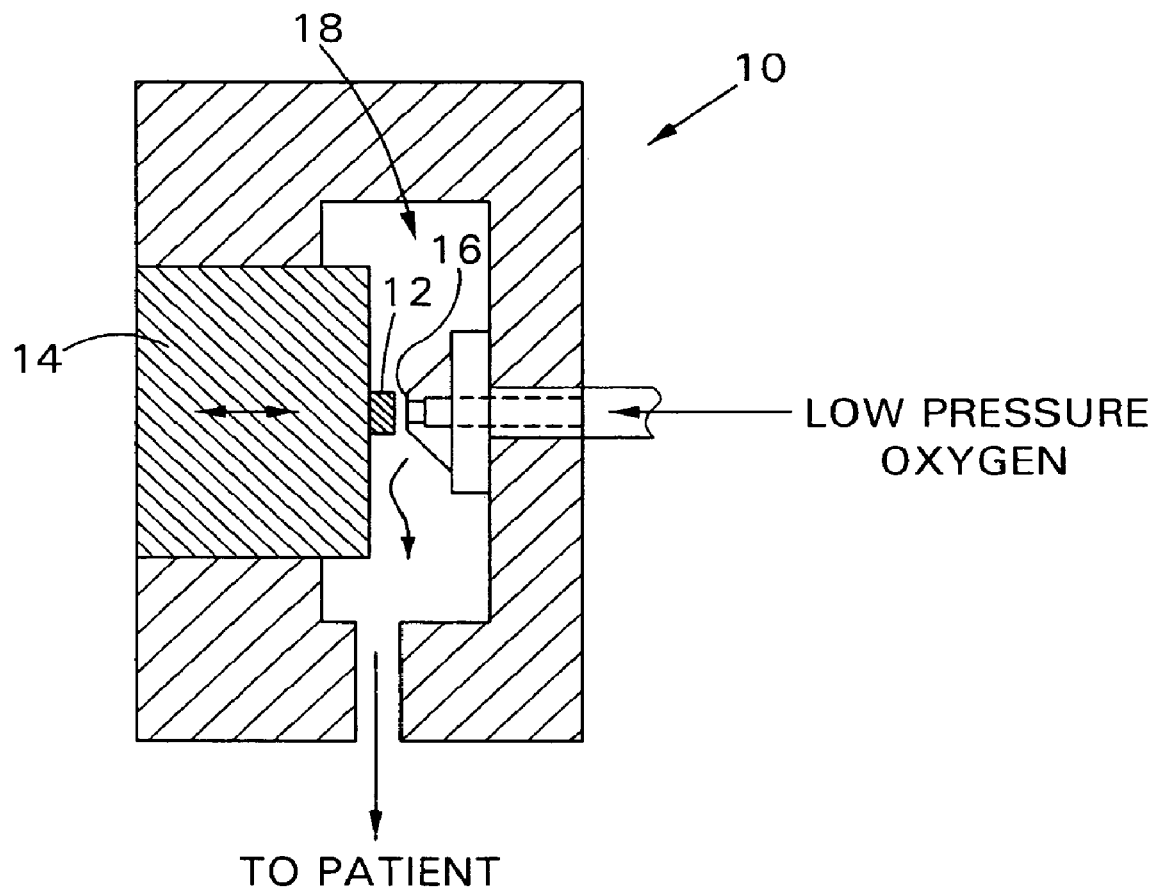
FIG. 1 is a schematic sectional drawing of a prior art electronic conserver for a regulator.

FIG. 1 is a schematic cross-section of a typical prior art electronic conserver 10. A solenoid 14 of a solenoid valve 18 controls a sealing member 12, such as a stopper made of rubber or similar material, relative to a nozzle 16. When the solenoid valve 18 is in the open position, oxygen flows through the nozzle 16 to the patient. At rest, the valve 18 is closed by the solenoid 14 thereby preventing the flow of oxygen to the patient. The solenoid 14 is actuated by a sensor (not shown) that senses a vacuum caused by the patient's inhalation, which results in the solenoid valve 18 opening. After a specific amount of time, the solenoid 14 is returned to its rest position, halting the flow of oxygen, and the system waits for the next inhalation trigger. A benefit of electronic conservers is that an electronic timing mechanism can provide accurate delivery of the gas to the patient. In addition, most electronic conservers can operate with a single-lumen cannula.

In electronic conservers, the opening of the nozzle 16 must be large enough to deliver the required amount of oxygen to the patient during the actuation period. For a system operating at a normal pressure of 15-25 PSI, the nozzle 16 typically has an opening that is about 3/64 inches in diameter. The solenoid valve 18 must therefore be able to seal the nozzle 16 against the gas pressure. At 22 PSI, for example, the solenoid 14 must provide at least about 0.04 pounds of resistance to seal the nozzle 16. That requires a fairly large solenoid unit, which has significant energy requirements. To meet those energy requirements, typical prior art conservers use a C or D-size battery. That battery is the largest single component of prior art conservers. Such batteries may only last for about one month.

Figure 2:
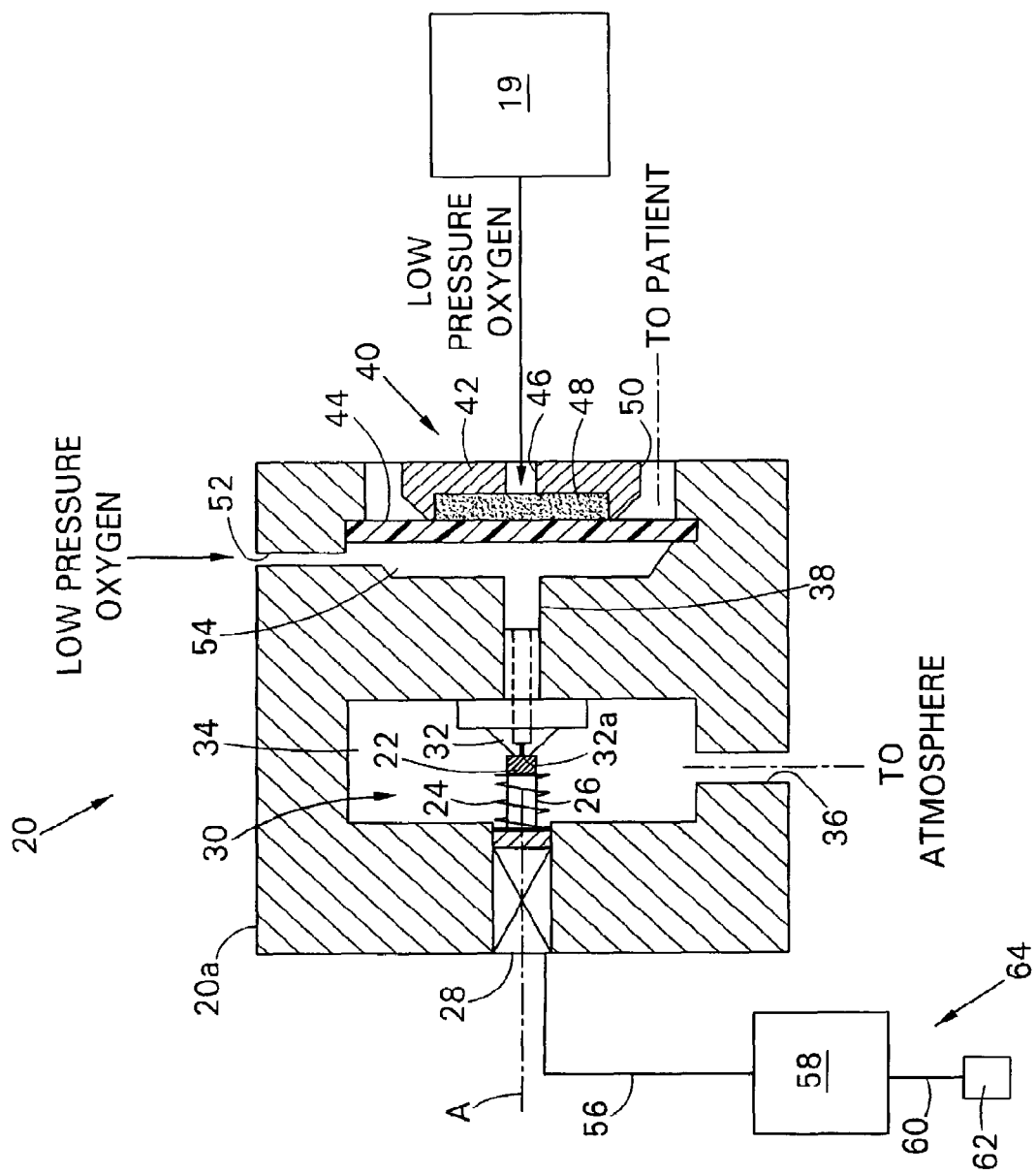
FIG. 2 is a schematic sectional drawing of an embodiment of a hybrid electro-pneumatic conserver regulator in the closed position.

FIG. 2 is a schematic cross-section of a particular hybrid oxygen conserver regulator 20. Examples of the core pneumatic architecture are described in U.S. Provisional Application No. 60/412,056, filed on Sep. 19, 2002, by LeNoir E. Zaiser, and U.S. application Ser. No. 10/666,115, filed on Sep. 19, 2003, by LeNoir E. Zaiser, the teachings of which are incorporated herein by reference.

Conserver 20 includes a housing 20a having a slave valve assembly 40 which receives low pressure oxygen from a pressure regulating portion 19. The pressure regulating portion 19 is in communication with a pressurized source of oxygen, such as from a supply tank which is often at about 2200 psi. The pressure regulating portion 19 typically includes a back pressure piston assembly, as is common in the art, which reduces the pressure of oxygen received from the pressurized source to between about 15-25 psi, typically about 22 psi. The slave valve assembly 40 controls the flow of the low pressure oxygen to the patient through a passage 50 and, in turn, is controlled by a solenoid operated pilot valve assembly 30. The slave valve assembly 40 is sized to deliver a sufficient amount of oxygen to the patient while the solenoid operated pilot valve assembly 30 is designed to use a minimal amount of energy while at the same time being capable of controlling the slave valve assembly 40. Typically, tubing is connected in communication with passage 50 and connected to the patient for delivering the oxygen through a mask or cannula.

The slave valve assembly 40 includes a slave valve nozzle 42 with a nozzle opening 46 and a filter 48 which receives oxygen from the pressure regulating portion 19. A slave valve member 44, typically a diaphragm, is engageable with the slave valve nozzle 42 for opening and closing the slave valve assembly 40. The operation of the slave valve member 44 is determined by the pressure within a timing chamber 54 adjacent to or against the slave valve member 44 which receives low pressure oxygen through an inlet passage 52. The timing chamber 54 is in communication with the solenoid operated pilot valve assembly 30 through a passage 38 in the housing 20a. The opening and closing of the pilot valve assembly 30 controls the pressure within timing chamber 54 and, therefore, the operation of the slave valve assembly 40.

The solenoid operated pilot valve assembly 30 has a pilot valve nozzle 32 and a pilot valve member 26 for engaging the pilot valve nozzle 32. The pilot valve member 26 is biased by a spring 24 against the pilot valve nozzle 32 to be normally closed and is opened by the activation of a solenoid 28. The pilot valve member 26 has a sealing surface or member 22 for sealing the pilot valve nozzle 32. The pilot valve assembly 30 is positioned in a cavity 34 within the housing 20a with the pilot valve nozzle 32 and the pilot valve member 26 extending into the cavity 34 from opposite sides. The cavity 34 is in communication with the atmosphere through a passage 36.

The solenoid 28 is controlled by a sensing circuit 64 which senses inhalation of the patient. The sensing circuit 64 includes a controller 58 that is connected to the solenoid 28 via line 56, and a sensor 62 which is in communication with controller 58 via line 60. The sensor 60 is positioned in a location to sense inhalation of the patient, such as in communication with the tubing connected to the patient.

In operation, referring to FIG. 2, at rest, the pilot valve assembly 30 and the slave valve assembly 40 of conserver 20 are both in the closed position so that low pressure oxygen provided by the pressure regulating portion 19 of conserver 20 is prevented from reaching the patient. In the solenoid operated pilot valve assembly 30, the solenoid 28 is deactivated so that the spring 24 biases the pilot valve member 26 against pilot valve nozzle 32 where the sealing member 22 seals the pilot valve nozzle 32 closed to prevent gas from passing through the opening 32a. The biasing force exerted by the spring 24 for closing the pilot valve member 26 is greater than the force exerted on the valve member 26 in the opposite direction by the gas or oxygen pressure within the pilot valve nozzle 32 over the small surface area provided by the diameter of the opening 32a of the nozzle 32. Since the pilot valve assembly 30 is closed, oxygen within the timing chamber cannot escape. As a result, the gas or oxygen pressure within the timing chamber 54 keeps the slave valve member 44 pressed against the slave valve nozzle 42 due to a force differential, because the closing force exerted by the gas pressure of the timing chamber 54 over the large surface area of the diaphragm of the slave valve member 44 is greater than the force exerted on the opposite side of the diaphragm by the gas pressure within the nozzle opening 46 of the slave valve nozzle 42 over the small surface area provided by the diameter of the nozzle opening 46.

Figure 3:
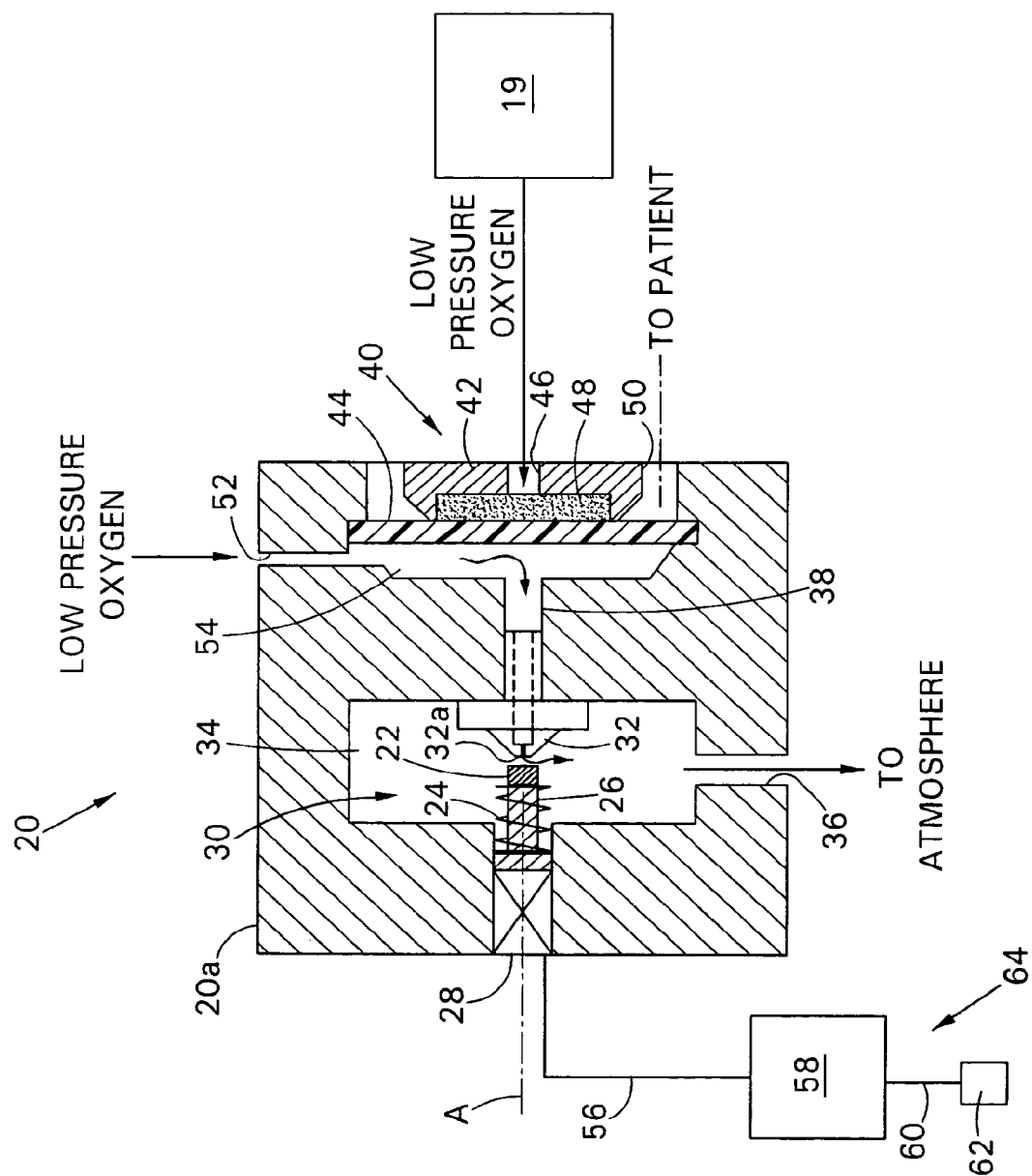
FIG. 3 is a schematic sectional drawings of the conserver regulator of FIG. 2 with only the solenoid operated pilot valve assembly being in the open position.

Referring to FIG. 3, when the patient takes a breath, the sensor 62 of sensing circuit 64 detects the vacuum caused by the patient's inhalation. The controller 58 then energizes and activates solenoid 28. The energized solenoid 28 overcomes the biasing force of the spring 24 and retracts the pilot valve member 26 away from the pilot valve nozzle 32. This opens the pilot valve assembly 30, which allows gas to exit the pilot valve nozzle 32. Once the pilot valve assembly 30 is opened, oxygen within the timing chamber 54 begins to exit the timing chamber 54 to the atmosphere via passage 38, pilot valve nozzle 32, cavity 34 and passage 36.

Figure 4:
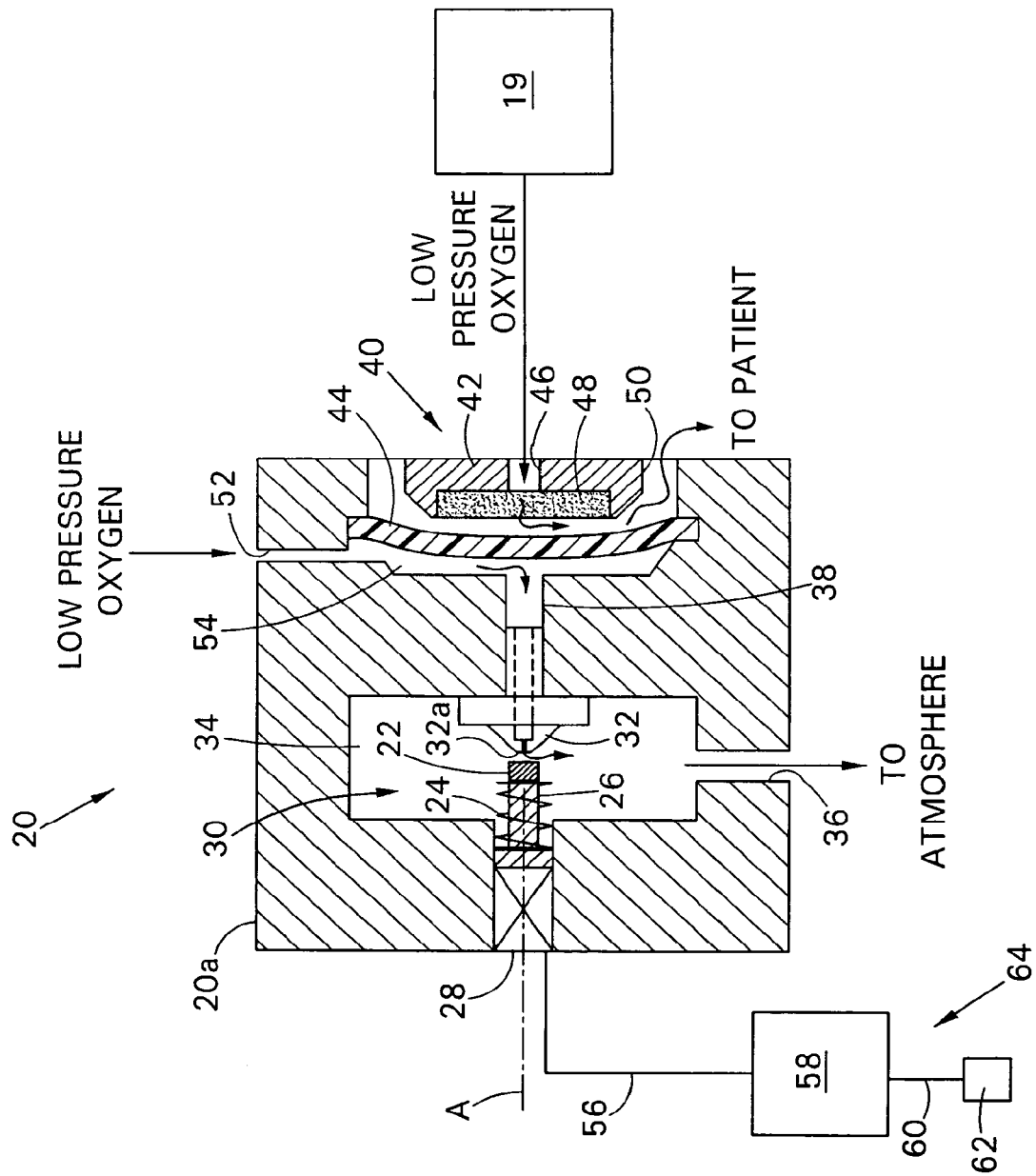
FIG. 4 is a schematic sectional drawing of the conserver regulator of FIG. 2 with both the solenoid operated pilot valve assembly and the pneumatic operated slave valve assembly being in the open position.

Referring to FIG. 4, as the oxygen within timing chamber 54 is vented to the atmosphere, the gas or oxygen pressure within the timing chamber 54 drops causing a reversed force differential on the slave valve member 44. The force exerted on the slave valve member 44 by the gas pressure within the nozzle opening 46 of the slave nozzle 42 becomes greater than the force exerted on the slave valve member 44 by the reduced gas pressure within the timing chamber 54. As a result, the gas pressure within the nozzle opening 46 pushes the slave valve member 44 off the slave valve nozzle 42 causing the slave valve member 44 to flex into the timing chamber 54, thereby opening the slave valve assembly 40. Once the slave valve assembly 40 is opened, low pressure oxygen provided by the pressure regulator portion 19 of conserver 20 can pass through slave valve nozzle 42 and passage 50 for delivery to the patient. After a timer in the controller 58 determines that a specific amount of time has passed, the controller 58 deactivates the solenoid 28 thereby allowing the spring 24 to bias the pilot valve member 26 back against the pilot valve nozzle 32 to close the pilot valve assembly 30. With the flow of oxygen through the pilot valve nozzle 32 terminated, the pressure within the timing chamber 54 repressurizes or rises back to the original or starting operating level. Consequently, this pressure forces the slave valve member 44 back against the slave valve nozzle 42 to block the flow through nozzle opening 46, thereby closing slave valve assembly 40 and terminating the flow of oxygen to the patient, such as shown in FIG. 2. The conserver 20 is then ready for the next breath by the patient.

A more detailed discussion of embodiments of conserver 20 now follows. The conserver 20 is typically operated with a single-lumen cannula, but alternatively can be operated with a dual-lumen cannula. The diaphragm of the slave valve member 44 forms one of the boundaries of the timing chamber 54 as well as operates as a valve member. The slave valve member 44 typically requires gas pressure in order to be closed. When there is no gas pressure, the slave valve member 44 can be apart from the slave valve nozzle 42. The sealing member 22 on the pilot valve member 26 is typically made of polymeric material suitable for sealing pilot valve nozzle 32, such as silicone rubber, or similar materials. In the embodiment shown in FIGS. 2-4, the pilot valve member 26 and the opening 32a of the pilot valve nozzle 32 are positioned along a longitudinal axis A where the pilot valve member 26 is a plunger that is reciprocated longitudinally along axis A towards and away from pilot valve nozzle 32 for opening and closing pilot valve assembly 30. The pilot valve nozzle 32 can have an opening 32a that is approximately 0.007 inches in diameter, so when the timing chamber 54 has a gas pressure of about 22 psi, the spring 24 only needs to overcome about 0.00085 lbs. of force against pilot valve member 26 exerted by the gas in the opening 32a of the pilot valve nozzle 32. The slave valve nozzle 42 can have an opening 46 that is about 0.048 inches in diameter so that the ratio of areas and gas pressure forces in the openings 46 and 32 is about 45:1, and is closer to about 47:1. In other embodiments, the pilot valve nozzle 32 can have an opening 32a that is about 0.007 inches in diameter and the slave valve nozzle 42 can have an opening 46 that is larger than 0.048 inches in diameter, for example, about 0.250 inches in diameter. In such an embodiment, the ratio of areas and gas pressure forces in the openings 46 and 32 is about 1290:1.

In comparison to the pilot valve nozzle 32, the nozzle opening in a conventional electronic conserver is typically about 3/64 inches in diameter for providing sufficient oxygen flow to the patient so that the force exerted by the gas at a pressure of 22 psi within such an opening against a valve member is about 0.04 lbs. and is over 45 times greater than in the opening 32a that is about 0.007 inches in diameter, because the ratio of the area of the nozzle openings is about 45:1. As a result, it can be seen that the solenoid 28 in conserver 20 can be sized many times smaller than the solenoid in a conventional electronic conserver. With the solenoid 28 being sized smaller than those in conventional electronic conservers, less energy is required for operation.

The solenoid energy efficiency can be directly proportional to the ratio of forces entered through the opening 32a in the pilot valve nozzle 32 relative to the opening in a standard electronic conserver. In embodiments having a pilot valve nozzle 32 with an opening 32a about 0.007 inches in diameter, the conserver 20 can have about a 45:1 solenoid efficiency ratio relative to a standard electronic conserver. That is, the solenoid 28 in the conserver 20 is about 45 times more energy efficient than a solenoid in a standard electronic conserver.

This means that a battery, that may only operate for one month in a conventional electronic conserver, can operate the conserver 20 for nearly four years. It also follows that a smaller battery, such as a camera battery, can be used to power the conserver 20 for an adequate period of time. Such advantages permit the conserver 20 to be both smaller and lighter than the conventional electronic conservers.

The conserver 20 allows for a variety of conserving ratios, defined as the ratio of the volume of oxygen delivered to the patient in comparison with the volume delivered by a standard, non-conserving regulator operating at the same flow rate. The conserver 20 can also be operated with a continuous, non-conserving flow at all flow settings, unlike conventional single-lumen conservers, most of which have only one continuous flow setting.

There are a number of variations that can be made to the mechanism with regard to the deactivation of the solenoid 28. In one such variation, the pilot valve member 26 can remain open for a fixed amount of time. To vary the amount of oxygen delivered to the patient, the flow rate of the oxygen can be adjusted. In another variation, the conserver 20 can deliver oxygen at a fixed flow rate, while the pilot valve member 26 remains open for a variable amount of time. This also allows the user to vary the amount of oxygen delivered to the patient. In yet another variation, the pilot valve member 26 can be opened using electronic means, and a pneumatic timer can be used to close the pilot valve member 26.

In another embodiment, the solenoid-controlled pilot valve member 26 can be replaced by a piezoelectric device. Circuitry can excite the piezo device, causing the piezo device to open the pilot valve nozzle, such as by expanding.

While this invention has been particularly shown and described with references to preferred embodiments thereof, it will be understood by those skilled in the art that various changes in form and details may be made therein without departing from the scope of the invention encompassed by the appended claims.

For example, although conserver 20 has been described for delivering oxygen to a patient, it is understood that conserver 20 can be used to deliver other gases, and to other desired destinations. Other therapeutic gases can be delivered such as nitrous oxide, or non-therapeutic gas can be delivered, such as lethal gases or gases for industrial uses. Although the components of the slave valve assembly 40 and the solenoid operated pilot valve assembly 30 have been shown in the figures to be aligned along axis A, alternatively, these components do not have to be in alignment with each other. In addition, it is understood that the slave valve assembly 40 and the solenoid operated pilot valve assembly 30 can have configurations other than those shown and described. For example, in some embodiments, the slave valve member can be a rigid member such as a piston having a large surface area acted on by gas pressure in the timing chamber 54 and a small surface area acted on by gas pressure in the nozzle opening 46. Also, gate valve configurations are possible. Other embodiments of the conserver 20 can have a solenoid operated pilot valve assembly including a spool that is shifted laterally relative to the gas flow for opening and closing the pilot valve assembly. Also, the solenoid operated pilot valve assembly can be located in a different housing than the slave valve assembly 40. Furthermore, it is understood that the diameter of the opening 32a of the pilot valve nozzle 32 can be varied to obtain the desired combination of energy efficiency and venting speed of timing chamber 55. Finally, it is understood that features of the present invention can be omitted or combined.

What is claimed is:

1. A gas conserver for delivering gas to a patient from a pressurized storage container, comprising:
   a gas regulator for providing gas at a regulated pressure;
   a slave valve assembly coupled to the gas regulator for receiving and controlling the flow of the regulated gas to a patient passage;

a timing chamber positioned adjacent to the slave valve assembly and coupled to the gas regulator, the timing chamber having an inlet for also receiving the regulated gas and an outlet to atmosphere; and an electronically operated pilot valve assembly in communication with the timing chamber for operating the slave valve assembly, when the pilot valve assembly is closed, gas pressure within the timing chamber acting on the slave valve assembly closes the slave valve assembly, and when the pilot valve assembly is open, gas exits the timing chamber through the outlet to atmosphere to reduce the gas pressure in the timing chamber thereby allowing the slave valve assembly to open and deliver the regulated gas to the patient passage.

2. The gas conserver of claim 1 in which the slave valve assembly comprises a slave valve nozzle and a slave valve member for engaging the slave valve nozzle, the gas pressure within the timing chamber acting on the slave valve member controlling the operation of the slave valve member.

3. The gas conserver of claim 2 in which the slave valve member is a diaphragm.

4. The gas conserver of claim 1 in which the electronically operated pilot valve assembly includes a piezoelectric device.

5. The gas conserver of claim 2 in which the electronically operated pilot valve assembly is a solenoid operated pilot valve assembly.

6. The gas conserver of claim 5 in which the solenoid operated pilot valve assembly comprises:
a pilot valve nozzle;
a pilot valve member for engaging the pilot valve nozzle; and
a solenoid for operating the pilot valve member.

7. The gas conserver of claim 6 in which the solenoid operated pilot valve assembly further comprises a spring for biasing the pilot valve member towards the pilot valve nozzle to be normally closed.

8. The gas conserver of claim 7 in which the pilot valve nozzle and the pilot valve member are aligned along a common axis, whereby the pilot valve member moves along the axis for engaging and disengaging from the pilot valve nozzle.

9. The gas conserver of claim 8 in which the gas regulator, the slave valve assembly, the timing chamber and the solenoid operated pilot valve assembly are positioned within a common housing, the timing chamber and the pilot valve nozzle being connected by a passage therebetween.

10. The gas conserver of claim 8 in which the slave and pilot valve nozzles each have an opening, the pilot valve nozzle opening being smaller than the slave valve nozzle opening for reducing the solenoid size and energy expended by the solenoid.

11. The gas conserver of claim 10 wherein the area of the slave valve nozzle opening is at least 45 times greater than the area of the area of the pilot valve nozzle opening.

12. The gas conserver of claim 11 in which the slave valve nozzle opening is at least about 0.048 inches in diameter and the pilot valve nozzle opening is about 0.007 inches in diameter.

13. The gas conserver of claim 1 in which the regulated gas is medical oxygen for delivery to a patient.

14. The gas conserver of claim 13 further comprising a sensing circuit for sensing inhalation by the patient for controlling the electronically operated pilot valve assembly.

15. A medical oxygen conserver for delivering medical oxygen to a patient, comprising:
a portable housing mountable to a portable oxygen storage tank;
a gas regulator within the housing for receiving medical oxygen from the storage tank and providing the medical oxygen at a regulated pressure;
a slave valve assembly positioned within the housing and coupled to the gas regulator for receiving and controlling the flow of regulated oxygen to a patient, the slave valve assembly having a slave valve nozzle and a slave valve member comprising a diaphragm for engaging the slave valve nozzle;
a timing chamber within the housing positioned adjacent to the slave valve member, the timing chamber having an inlet coupled to the gas regulator for also receiving the regulated oxygen and an outlet to atmosphere; and
a solenoid operated pilot valve assembly positioned within the housing and in communication with the timing chamber by a passage therebetween for operating the slave valve assembly, the solenoid operated pilot valve assembly comprising a pilot valve nozzle, a pilot valve member for engaging the pilot valve nozzle, a solenoid for operating the pilot valve member, and a spring for biasing the pilot valve member towards the pilot valve nozzle such that the pilot valve assembly is normally closed, and when the pilot valve assembly is closed, oxygen pressure within the timing chamber acting on the slave valve member closes the slave valve assembly, and when the pilot valve assembly is open, oxygen exits from the timing chamber through the outlet to atmosphere to reduce the oxygen pressure in the timing chamber thereby allowing the slave valve assembly to open and deliver the regulated oxygen to the patient, the slave and pilot valve nozzles each having an opening, the pilot valve nozzle opening being smaller than the slave valve nozzle opening for reducing the solenoid size and energy expended by the solenoid.

16. The medical oxygen conserver of claim 15 in which the pilot valve nozzle and the pilot valve member are aligned along a common axis, whereby the pilot valve member moves along the axis for engaging and disengaging from the pilot valve nozzle.

17. The medical oxygen conserver of claim 16 wherein the area of the slave valve nozzle opening is at least 45 times greater than the area of the area of the pilot valve nozzle opening.

18. The medical oxygen conserver of claim 17 in which the slave valve nozzle opening is at least about 0.048 inches in diameter and the pilot valve nozzle opening is about 0.007 inches in diameter.

19. The medical oxygen conserver of claim 15 further comprising a sensing circuit for sensing inhalation by the patient for controlling the electronically operated pilot valve assembly.

20. A method of conserving gas from a pressurized storage container for delivery to a patient, comprising:
from a gas regulator, providing gas at a regulated pressure;
receiving and controlling the flow of the regulated gas to a patient passage with a slave valve assembly coupled to the gas regulator;
operating a timing chamber adjacent to the slave valve assembly and coupled to the gas regulator, the timing chamber having an inlet for also receiving the regulated gas and an outlet to atmosphere; and
operating the slave valve assembly with an electronically operated pilot valve assembly which is in communication with the timing chamber, when the pilot valve assembly is closed, gas pressure within the timing chamber acting on the slave valve assembly closes the slave valve assembly, and when the pilot valve assembly is open, gas exits the timing chamber through the outlet to atmosphere to reduce the gas pressure in the timing chamber thereby allowing the slave valve assembly to open and deliver the regulated gas to the patient passage.

21. The method of claim 20 in which the slave valve assembly comprises a slave valve nozzle and a slave valve member for engaging the slave valve nozzle, the method further comprising controlling the operation of the slave valve member with the gas pressure acting on the slave valve member.

22. The method of claim 21 further comprising forming the slave valve member from a diaphragm.

23. The method of claim 20 further comprising providing the electronically operated pilot valve assembly with a piezoelectric device.

24. The method of claim 21 further comprising forming the electronically operated pilot valve assembly as a solenoid operated pilot valve assembly.

25. The method of claim 24 further comprising providing the solenoid operated pilot valve assembly with: a pilot valve nozzle; a pilot valve member for engaging the pilot valve nozzle; and a solenoid for operating the pilot valve member.

26. The method of claim 25 further comprising biasing the pilot valve member towards the pilot valve nozzle with a spring to be normally closed.

27. The method of claim 26 further comprising aligning the pilot valve nozzle and the pilot valve member along a common axis, whereby the pilot valve member moves along the axis for engaging and disengaging from the pilot valve nozzle.

28. The method of claim 27 further comprising operating the gas regulator, the slave valve assembly, the timing chamber and the solenoid operated pilot valve assembly within a common housing, the timing chamber and the pilot valve nozzle being connected by a passage therebetween.

29. The method of claim 27 further comprising providing the slave and pilot valve nozzles each with an opening, the pilot valve nozzle opening being smaller than the slave valve nozzle opening for reducing the solenoid size and energy expended by the solenoid.

30. The method of claim 29 wherein the area of the slave valve nozzle opening is at least 45 times greater than the area of the area of the pilot valve nozzle opening.

31. The method of claim 30 wherein the slave valve nozzle opening is at least about 0.048 inches in diameter and the pilot valve nozzle opening is about 0.007 inches in diameter.

32. The method of claim 20 further comprising delivering medical oxygen to a patient.

33. The method of claim 32 further comprising sensing inhalation by the patient with a sensing circuit for controlling the electronically operated pilot valve assembly.

34. A method of conserving medical oxygen with a medical oxygen conserver comprising:
mounting a portable housing to a portable oxygen storage tank;
with a gas regulator within the housing, receiving medical oxygen from the storage tank and providing the medical oxygen at a regulated pressure;
receiving and controlling the flow of regulated oxygen to a patient with a slave valve assembly positioned within a housing and coupled to the gas regulator, the slave valve assembly having a slave valve nozzle and a slave valve member comprising a diaphragm for engaging the slave valve nozzle;
positioning a timing chamber within the housing adjacent to the slave valve member, the timing chamber having an inlet coupled to the gas regulator for also receiving the regulated oxygen and an outlet to atmosphere; and
operating the slave valve assembly with a solenoid operated pilot valve assembly positioned within the housing and in communication with the timing chamber by a passage therebetween, the solenoid operated pilot valve assembly comprising a pilot valve nozzle, a pilot valve member for engaging the pilot valve nozzle, a solenoid for operating the pilot valve member, and a spring for biasing the pilot valve member towards the pilot valve nozzle such that the pilot valve assembly is normally closed, and when the pilot valve assembly is closed, oxygen pressure within the timing chamber acting on the slave valve member closes the slave valve assembly, and when the pilot valve assembly is open, oxygen exits from the timing chamber through the outlet to atmosphere to reduce the oxygen pressure in the timing chamber thereby allowing the slave valve assembly to open and deliver the regulated oxygen to the patient, the slave and pilot valve nozzles each having an opening, the pilot valve nozzle opening being smaller than the slave valve nozzle opening for reducing the solenoid size and energy expended by the solenoid.

35. The method of claim 34 further comprising aligning the pilot valve nozzle and the pilot valve member along a common axis, whereby the pilot valve member moves along the axis for engaging and disengaging from the pilot valve nozzle.

36. The method of claim 35 wherein the area of the slave valve nozzle opening is at least 45 times greater than the area of the area of the pilot valve nozzle opening.

37. The method of claim 36 wherein the slave valve nozzle opening is at least about 0.048 inches in diameter and the pilot valve nozzle opening is about 0.007 inches in diameter.

38. The method of claim 34 further comprising sensing inhalation by the patient with a sensing circuit for controlling the electronically operated pilot valve assembly.

39. The conserver of claim 1 wherein the patient passage is couplable to a single-lumen cannula.

40. The method of claim 20 further comprising coupling the patient passage to a single-lumen cannula.

41. A method of fabricating a gas conserver for delivering gas to a patient from a pressurized storage container, comprising:
forming a coupling to a gas regulator for providing gas at a regulated pressure;
forming a slave valve assembly coupled to the gas regulator for receiving and controlling the flow of the regulated gas to a patient passage;
forming a timing chamber positioned adjacent to the slave valve assembly and coupled to the gas regulator, the timing chamber having an inlet for also receiving the regulated gas and an outlet to atmosphere; and
forming an electronically operated pilot valve assembly in communication with the timing chamber for operating the slave valve assembly, when the pilot valve assembly is closed, gas pressure within the timing chamber acting on the slave valve assembly closes the slave valve assembly, and when the pilot valve assembly is open, gas exits the timing chamber through the outlet to atmosphere to reduce the gas pressure in the timing chamber thereby allowing the slave valve assembly to open and deliver the regulated gas to the patient passage.

42. A method of fabricating medical oxygen conserver for delivering medical oxygen to a patient, comprising:
forming a portable housing to mount to a portable oxygen storage tank;

installing a gas regulator within the housing for receiving medical oxygen from the storage tank and providing the medical oxygen at a regulated pressure;

positioning a slave valve assembly within the housing and coupled to the gas regulator for receiving and controlling the flow of regulated oxygen to a patient, the slave valve assembly having a slave valve nozzle and a slave valve member comprising a diaphragm for engaging the slave valve nozzle;

positioning a timing chamber within the housing adjacent to the slave valve member, the timing chamber having an inlet coupled to the gas regulator for also receiving the regulated oxygen and an outlet to atmosphere; and positioning a solenoid operated pilot valve assembly within the housing and in communication with the timing chamber by a passage therebetween for operating the slave valve assembly, the solenoid operated pilot valve assembly comprising a pilot valve nozzle, a pilot valve member for engaging the pilot valve nozzle, a solenoid for operating the pilot valve member, and a spring for biasing the pilot valve member towards the pilot valve nozzle such that the pilot valve assembly is normally closed, and when the pilot valve assembly is closed, oxygen pressure within the timing chamber acting on the slave valve member closes the slave valve assembly, and when the pilot valve assembly is open, oxygen exits from the timing chamber through the outlet to atmosphere to reduce the oxygen pressure in the timing chamber thereby allowing the slave valve assembly to open and deliver the regulated oxygen to the patient, the slave and pilot valve nozzles each having an opening, the pilot valve nozzle opening being smaller than the slave valve nozzle opening for reducing the solenoid size and energy expended by the solenoid.

43. The method of claim 41 wherein forming the slave valve assembly comprises forming a slave valve nozzle and a slave valve member for engaging the slave valve nozzle, such that gas pressure within the timing chamber acts on the slave valve member to control operation of the slave valve member.

44. The method of claim 41 further comprising including a piezoelectric device in the electronically operated pilot valve assembly.

45. The method of claim 41 further comprising forming the electronically operated pilot valve assembly as a solenoid operated pilot valve assembly.

46. The method of claim 41 further comprising providing a sensing circuit sensing an inhalation by a patient and controlling the electronically operated pilot valve assembly for delivering medical oxygen to the patient.

47. The method of claim 42 further comprising aligning the pilot valve nozzle and the pilot valve member along a common axis, whereby the pilot valve member is movable along the axis for engaging and disengaging from the pilot valve nozzle.

48. The method of claim 47 wherein the area of the slave valve nozzle opening is at least 45 times greater than the area of the area of the pilot valve nozzle opening.

49. The method of claim 42 further comprising providing a sensing circuit for sensing inhalation by the patient and controlling the electronically operated pilot valve assembly.

* * * * *